United States Patent [19]

Golebiowski et al.

[11] 4,019,969

[45] Apr. 26, 1977

[54] METHOD OF MANUFACTURING CATALYTIC TUBES WITH WALL-SUPPORTED CATALYST, PARTICULARLY FOR STEAM REFORMING OF HYDROCARBONS AND METHANATION

[75] Inventors: Andrzej Golebiowski; Stanislawa Paluch; Zdzislaw Janecki; Alfred Polanski; Waclaw Hennel, all of Pulawy; Jerzy Zielinski, Warszawa; Cezary Warzec, Warszawa; Wojciech Lisowski, Warszawa, all of Poland

[73] Assignee: Instytut Nawozow Sztucznych, Pulawy, Poland

[22] Filed: Nov. 17, 1975

[21] Appl. No.: 633,018

[52] U.S. Cl. .............................. 204/26; 204/37 R; 204/38 R

[51] Int. Cl.² ...................... C25D 5/50; C25D 7/04

[58] Field of Search ............. 204/38 R, 38 S, 38 C, 204/37 R, 26

[56] References Cited

UNITED STATES PATENTS 3,357,916   12/1967   Smith ................................ 208/120
3,790,454   2/1974   Henderson et al. ............. 204/38 R
3,884,772   5/1975   Shiga .................................. 204/16

*Primary Examiner*—T. M. Tufariello

[57] ABSTRACT

This invention relates to a method of manufacturing catalytic tubes with wall-supported catalyst particularly for steam reforming of hydrocarbons and methanation, wherein at first a porous layer of metal sponge is laid on the tube surface by the known method of electrolysis, wherein said tube is permanently filled with electrolyte and a shield mounted on the anode is raised step by step or in continuous manner during electrolysis. Said tube constitutes a cathode during electrolysis, and a metal bar placed in the axis of the tube forms an anode. The tube is roasted at a temperature of 800°–1200° C, then salts are introduced into the sponge, which after roasting yield metal oxides irreducible in the presence of a hydrogen and salts, which yield reducible metal oxides, and coating the layer with salts is performed by known methods using aqueous solutions of salts, and after coating the roasting is carried out.

17 Claims, No Drawings

METHOD OF MANUFACTURING CATALYTIC TUBES WITH WALL-SUPPORTED CATALYST, PARTICULARLY FOR STEAM REFORMING OF HYDROCARBONS AND METHANATION

A method of manufacturing catalytic tubes according to the invention is applicable in constructing chemical catalytic reactors of the new type, in which the catalyst forms a thin layer closely connected with a reactor wall. Such a catalyst was named "wall — supported" and the wall, together with the catalyst, was named "catalystic tube".

This type of reactor has been known, for a short time, from the patent literature, in particular from U.S. Pat. Nos. 3,271,326; 3,357,916; 3,499,797; 3,672,847 and from French Pat. No. 1,465,414. The reactors of the new type are very advantageous in the case of gaseous reactions requiring intensive heat exchange, in particular reforming of hydrocarbons with steam and methanation. The superiority of these reactors in relation to the known, commonly used reactors filled with a granular catalyst bed consists above all in making heat circulation easier. Namely heat transfer between the environment and the catalyst in the new-type reactors takes place only through a tube wall coated with a catalyst layer, independently of whether the heat is to be supplied for the reaction or taken therefrom. On the other hand in commonly used reactors the heat must also be transferred from a wall surface to the catalyst through the gas, which results in a considerable decrease of temperature, the latter is always disadvantageous to the course of the process.

It is an additional advantage of the new-type catalytic reactors to have the hydraulic resistance considerably reduced in comparison with the resistance of known reactors filled with a granular catalyst.

In spite of these advantages, reactors with wallsupported catalyst have not been hitherto employed in industry. Such a situation results from the lack of a method of fabricating a catalyst of high quality and at the same time connected with a wall, sufficiently durably at a high temperature. The difficulty consists in that, for such reactions as steam reforming and methanation a catalyst should contain a ceramic base. On the other hand any ceramic materials, which can be used as such a base coated on a metal wall, fall away from this wall as a result of temperature changes because of their different thermal expansion.

In the cited patent literature, which is a principal source of commonly accessible information about chemical reactors with a wall-supported catalyst, only in three cases have methods of fabricating the wall-supported catalyst been given. In U.S. Pat. Nos. 3,271,326 and 3,499,797 a catalyst which is entirely metallic without a ceramic base is proposed. It is known from the general knowledge about catalysts that such a catalyst would not be durable owing to recrystallization of the metallic catalytically active substances. It is only when these substances are placed on a ceramic base, in other words on a so-called "carrier" e.g. from a porous $Al_2O_3$ or MgO, that recrystallization is prevented, which results in durability.

In a no French Pat. No. 1,465,414 the hope was expressed that sufficiently tight connection of a catalytic porous ceramic material with a metal wall will be achieved after previous pickling of the latter with an acid. This idea did not prove correct during experiments.

The above — described problem of making catalytic tubes which satisfy the considered requirements can be resolved according to the invention when by producing a metal sponge on the wall surface by electrolysis and subsequently introducing ceramic and catalytically active substances into this sponge.

In the process of electrolysis a wall to be coated with a catalyst forms a negative electrode. By means of a suitable solution and appropriately chosen positive electrode, e.g. a nickel one, coating the wall with a metal is carried out under such process parameters that make a depositing metal layer suitably porous i.e. formed into a sponge. It was found that the structure of the sponge being made depends particularly on the electrolyte temperature. In the case of using nickel as a sponge material, the best result is obtained in the range of temperatures from 15 to 80° C. It was also discovered that in order to obtain an equal thickness of sponge layer all along the tube, it is very advantageous to arrange the tube, together with the other electrode, obliquely or vertically, and to raise the electrolyte progressively during electrolysis.

It is also advantageous to have all the tube permanently filled with the electrolytic solution and to raise a special anode shield (step by step or in a continuous manner), when the electrolyte circulating between a thermostabilizing tank and the tube. On the other hand, in order to obtain an especially firm connection of the sponge with the tube wall it is necessary to prepare a sponge denser on the tube surface than farther from it. The density and porosity of the metal sponge depend not only on the current density and electrolyte temperature but also on the electrolyte pH-value and can be controlled by these three parameters. The best results are obtained with current densities ranging from 10 to 60 $A/dcm^2$ and electrolyte pH-values ranging from 2.2 to 6.8.

When developing a method according to the invention it was found that mechanical resistance of the catalyst can be additionally increased by roasting the tube at a temperature of 800°– 1200° C after preparing the metal sponge, but before impregnating it with the described solutions.

In order to introduce ceramic and catalytically active substances into the prepared sponge, an impregnation of the sponge with aqueous solutions of appropriate salts is employed according to the invention. After impregnating the sponge is exsiccated and roasted. It is especially advantageous to introduce into the sponge first a salt which when decomposed by roasting, yields oxides which are irreducible during reactor operation, and afterwards another salt which yields reducible oxides of metals which catalyze the given reaction. Transforming the latter oxides into crystallites of a catalytically active metal is carried out by reduction as early as during reactor operation. In the method according to the invention any metals catalyzing given reaction can be used, e.g. in the case of reforming and methanation: Ru, Tr, Th, Ni, Co, Os, Pt, Fe, Mo, Pd, Ag, Though electrolysis constitutes the known domain of physics and technology, and the method of introducing salts into a porous body according to the invention has been known in chemical preparations and catalysis for a long time, the application of these two known processes for manufacturing the discussed catalytic tubes yields a product of a hitherto unknown quality. Namely it appeared that the connection of the metal sponge with the tube wall obtained by the method according to the invention and placing ceramic substances in the sponge was durable and resistant to greater and more violent temperature changes than could possibly occur during reactor operation. It appeared also that irreducible oxides introduced into the electrolytic metal sponge protected crystallites of a catalytically active metal against recrystallization just as in the known catalyst. The surface of the catalytically active metal obtained at the same time was sufficient for economical accomplishment of steam reforming of hydrocarbons. Thus the quality of catalytic tubes obtained by the method according to the invention makes it already possible to provide the industry with the new-type reactors i.e. reactors with a wall-supported catalyst.

EXAMPLE 1.

A reactor is to be used for reforming of methane with steam in order to obtain a gas rich in a hydrogen. Tubes, from which catalytic tubes are to be made, are produced from an austenitic chromium-nickel steel and have an external diameter of 42 mm and an internal one of the 30 mm. Every diameter of tubes is arranged vertically, in its axis a nickel bar having a diameter of 6 mm is placed and the whole is dipped not deeply in an electrolyte of the composition:

| | |
|---|---|
| $NiSO_4 . 7H_2O$ | 80 g/l |
| $NH_4Cl$ | 50 g/l |
| $NaCl$ | 200 g/l |

A direct current having a voltage of 3.5 V is applied on the bar and tubes as electrodes. The electrolyte level was raised progressively with simultaneous adjustment of the speed of raising to the speed of complete dissolving of the bar. The current density on the cathode was about 20 $A/dcm^2$. The electrolyte temperature was about 37° C. The tubes were roasted at a temperature of 1050° C in a hydrogen atmosphere for 2 hours.

As a result, a layer of electrolytic metallic sponge was obtained, said layer being very regular all along the tube, resistant and closely adherent to the internal tube surface. The thickness of the layer was of 0.6 mm, porosity of 55% and roughness coefficient of 250. Then, after scouring the inside of the tube, the latter was several times filled with a solution of aluminum nitrate and roasted at temperatures from 500° to 1000° C.

The similar procedure was repeated twice, using a nickel nitrate. An analysis of the finished wall-supported catalyst showed, that the percentage by mass of porous $Al_2O_3$ in the wall-supported catalyst as a whole was about 6% the porosity of the catalyst was 41%, the internal surface was 12 $m^2/g$.

EXAMPLE 2.

A tube made of austenitic chromium-nickel steel, having an external diameter of 42 mm and an internal diameter of 30 mm, was arranged vertically and a nickel bar of a diameter of 6 mm within the insulating shield was placed in the tube axis. The whole was connected to an electrolyte-containing tank, said electrolyte having a composition as in Example 1 in such a manner as to enable the solution to circulate permanently between the tank and the tube and to keep the electrolyte temperature constant at a level of 80° C. A direct current having a cathode density of 10 $A/dcm^2$ was applied on the bar and tube. The anode shield was raised step by step in order to deposit the metal sponge on the subsequent tube segments. The electrolyte pH-value was kept constant of at 2.2 throughout the electrolysis. Afterwards the tube was roasted at a temperature of 1050° C for 2 hours in a hydrogen atmosphere. As a result, a layer of electrolyte metal sponge was obtained, said layer being regular all along the tube and closely adherent to the internal tube surface. The thickness of the layer was 0.5 mm and the porosity 50%. Then a ceramic and active substance was deposited on the tube by the method given in Example 1. The tube with the wall-supported catalyst deposited presented very good catalystic properties in reforming methane with stearn.

EXAMPLE 3.

A wall-supported catalyst was obtained as in Example 2 but a metal sponge was obtained under different conditions, namely at the electrolyte temperature of 15° C, current density of 60 $A/dcm^2$ and the electrolyte pH-value of 6.8. The catalyst obtained presented a porosity of about 70% and catalystic properties not much different from those of the catalyst obtained in Example 2.

EXAMPLE 4.

A metal sponge was deposited on a tube, having an external diameter of 42 mm and an internal diameter of 30 mm, by the method given in Example 2, and the electrolyte temperature was kept at a level of 50° C, current density of 30 $A/dcm^2$ and electrolyte pH-value of 5.9. Afterwards the tube was roasted at a temperature of 1050° C for 2 hours in a reducing atmosphere. A sponge layer having a thickness of 0.5 mm and porosity of 65% was obtained. A ceramic and active substance was then deposited on the tube by the method given in Example 1. The wall-supported catalyst obtained presented a good activity in the process of producing hydrogen from methane and steam.

EXAMPLE 5.

A tube with deposited nickel sponge, obtained as in Example 1, was filled twice with a solution of Aluminum nitrate, then roasted at temperatures of 1000° and 500° C. After cooling it was filled with a 10% solution of rhodium nitrate and after removing the liquid in excess and cooling reduction was carried out at a temperature of 800° C for 1 hour and after cooling down to 100° C a passivation in a mixture of $N_2$ and $O_2$.

The analysis of the prepared wall-supported catalyst showed that the percentage by mass of the porous $Al_2O_3$ in the whole of the wall-supported catalyst was about 6%, the catalyst porosity about 40% and the specific surface 15 $m^2/g$.

EXAMPLE 6.

A tube with deposited metal sponge, obtained as in Example 1, was roasted at a temperature of 800° C for 4 hours in hydrogen atmosphere. After cooling a ceramic and active substance was deposited by the method given in Example 1. The wall-supported catalyst was obtained, having a porosity of 50% closely adherent to the tube, and having a specific surface of about 13 $m^2/g$.

EXAMPLE 7.

A tube with deposited metal sponge, obtained as in Example 1, was roasted at a temperature of 1200° C for 1 hour in a hydrogen atmosphere. After cooling a ceramic and active substance was deposited by the method given in Example 1. The catalyst obtained had a porosity of about 45% and a specific surface of 10 m$^2$/g.

We claim:

1. A method of manufacturing a catalytic tube with wall-supported catalyst particularly for steam reforming of hydrocarbons and methanation, comprising depositing a porous coating of metal sponge on the tube surface by electrolysis, impregnating the sponge with aqueous solutions of salts which after roasting yield metal oxides irreducible in the presence of hydrogen and of salts, which yield reducible metal oxides, and roasting the impregnated sponge coated tube to form metal oxides deposited in said metal sponge.

2. The method of claim 1, in which the tube constitutes the cathode during electrolysis, and a metal bar placed in the axis of the tube constitutes the anode, wherein said tube is permanently filled with electrolyte and a shield mounted on the anode is raised step by step or in a continuous manner during electrolysis.

3. The method of claim 1, wherein the electrolyte circulates between a thermostabilizing tank and the tube on which the porous metal sponge is deposited.

4. The method of claim 1, wherein nickel is the metal from which the sponge layer is prepared, and the electrolysis is performed in the range of temperatures from 15° to 20° C.

5. The method of claim 1, in which the tube constitutes the cathode during electrolysis, and a metal bar placed in the axis of the tube constitutes the anode, wherein the tube as well as said bar are arranged vertically or obliquely, and the electrolyte level is raised progressively during electrolysis.

6. The method of claim 1, wherein during preparation of the first portion of the sponge layer, directly adherent to the wall, such conditions of electrolysis are used as to obtain a sponge of higher density than the sponge obtained when preparing the remaining portion of the sponge layer.

7. The method of claim 1, wherein the tube is roasted at a temperature of 800°–1200° C after preparing the metal sponge but before introducing salts into this sponge.

8. The method of claim 1, wherein the electrolysis proceeds with current densities ranging from 10 to 60 A/dcm$^2$.

9. The method of claim 1, wherein the electrolyte pH-value is kept at a level of 2.2–6.8 during electrolysis.

10. The method of claim 2 wherein the electrolyte circulates between a thermostabilizing tank and the tube; the tube and the bar are arranged vertically or obliquely; the electrolysis conditions are selected so as to obtain a first portion of sponge layer directly adherent to the wall of higher density than remaining portion of the sponge layer; the current density ranges from 10 to 60 A/dcm$^2$; and the pH is maintained at a level of 2.2–6.8 during electrolysis.

11. The method of claim 10, wherein the tube is roasted at a temperature of 800°–1200° C after preparing the metal sponge but before introducing salts into this sponge.

12. The method of claim 10, wherein nickel is the metal from which the sponge layer is prepared, and the electrolysis is performed in the range of temperatures from 15° to 20° C.

13. The method of claim 11, wherein nickel is the metal from which the sponge layer is prepared, and the electrolysis is performed in the range of temperatures from 15° to 20° C.

14. The catalytic tube obtained by the method of claim 1.

15. The catalytic tube obtained by the method of claim 4.

16. The catalytic tube obtained by the method of claim 10.

17. The catalytic tube obtained by the method of claim 11.

* * * * *